(12) United States Patent
Gott et al.

(10) Patent No.: US 7,527,806 B2
(45) Date of Patent: May 5, 2009

(54) PERSONAL CARE ARTICLE WITH DISTINCT ACTIVE ZONE

(75) Inventors: Robert Edward Gott, Norwalk, CT (US); Ewa Padlo, Derby, CT (US); Craig Stephen Slavtcheff, Guilford, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 1470 days.

(21) Appl. No.: 10/134,207

(22) Filed: Apr. 26, 2002

(65) Prior Publication Data

US 2003/0206940 A1 Nov. 6, 2003

(51) Int. Cl.
*A61F 13/00* (2006.01)
*A61K 9/70* (2006.01)
(52) U.S. Cl. .................. 424/443; 424/401; 424/445
(58) Field of Classification Search .......... 424/402, 424/401, 70.1, 489, 488, 490, 448, 449, 443, 424/445, 69, 414
See application file for complete search history.

(56) References Cited

U.S. PATENT DOCUMENTS 4,987,632 A * 1/1991 Rowe et al. ............. 15/104.93
5,972,361 A * 10/1999 Fowler et al. ............. 424/402
6,231,719 B1 * 5/2001 Garvey et al. ............. 162/109

FOREIGN PATENT DOCUMENTS

WO      WO 01/54661 A1 * 8/2001
WO      WO0154661 A1 * 8/2001

OTHER PUBLICATIONS

International Search Report No. PCT/EP 03/03465 dated Jul. 31, 2003, 4 pp.

* cited by examiner

*Primary Examiner*—Michael G Hartley
*Assistant Examiner*—Micah-Paul Young
(74) *Attorney, Agent, or Firm*—Alan A. Bornstein

(57) ABSTRACT

A disposable, single-use, personal care article is disclosed having an active zone, an adjacent non-active zone, and interface therebetween; a benefit agent releasably associated with the active zone; a carrier solvent and optionally a visual indicator associated with the active zone. In one embodiment, the benefit agent, the carrier solvent, and a dye indicator are combined and applied as stripes on the article. The stripes will not substantially bleed into the adjacent non-active zone and will disappear during use of the article indicating that the benefit agent has been transferred to the skin or hair of the user.

29 Claims, 3 Drawing Sheets

PERSONAL CARE ARTICLE WITH DISTINCT ACTIVE ZONE

BACKGROUND

1. Field of the Invention

The invention relates to single use, disposable, personal cleansing products, and more specifically to an article with a distinct active zone.

2. Description of the Related Art

Personal cleansing products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use. Personal cleansing products have also been combined with water insoluble substrates to improve convenience to the user.

Visual indicators such as color has been used to denote the distinction of active zones and the depletion of active substances associated with various substrates. U.S. Pat. No. 4,311,479 titled Method of Indicating the Presence of an Impregnant in a Substrate, issued to D. Fenn et al. on Jan. 19, 1982 discloses a method for detecting the presence of an impregnant, e.g. an antimicrobial composition in a cloth to provide visual evidence of the continuing activity of the impregnant. Portions of the impregnated cloth are dyed with an indicator dye which bonds preferentially to the antimicrobial composition so that when the antimicrobial composition is exhausted, the dye will disappear from the cloth.

U.S. Pat. No. 4,678,704 titled Impregnated Substrate Incorporating An Indicator Dye issued to A. Fellows on Jul. 1, 1987 discloses an impregnated fabric material that has been bonded to an active cationic impregnant, and an anionic indicator dye in combination with a further cationic component also applied to the fabric material, wherein the dye bonds to the second cationic component more readily than to the fabric The second cationic component competes with the impregnant for bonding to the dye. In the case of a wiping cloth, the dye acts as an indicator the disappearance of which indicates depletion of the active component with use.

U.S. Pat. No. 4,987,632 titled Wiping Article, issued to Rowe et al. on Jan. 29, 1991 discloses a substantially dry-to-the-touch wiping article which is suitable for use in cleaning soiled surfaces in the presence of water, and that has a water absorbent substrate impregnated with a detergent active compound and sandwiched by a moisture barrier. The moisture barrier is applied to the article's surface in the form of a design pattern, decorative feature or logo. The detergent active material or the moisture barrier can comprise a water-soluble dyestuff or colorant and a perfume, the disappearance of which can signal exhaustion of the material. DT 2625176A to Schickdenz, published in December 1977, discloses a wiping cloth with an active detergent distributed in a pattern such as in the form of lines, etc., onto the cloth and separated from the untreated areas of the cloth by a hydrophobic substance or boundary strip. U.S. Pat. No. 4,601,938 to Deacon et al. issued on Jul. 22, 1986 discloses a wet wiping article impregnated with a liquid composition such as a skin treatment composition in specific areas where migration of the liquid is prevented by means of a repeating pattern of liquid repellant barriers. However, there is no disclosure or suggestion in either Rowe et al., Schickdenz, or Deacon et al. of the effect of carrier solvent on migration or bleeding of active components in the article to adjacent zones when no liquid or moisture barrier is used.

U.S. Pat. No. 5,293,648, titled Tag For Visually Indicating Loss Of A Protective Agent, issued to R. Finley on Mar. 15, 1994 discloses an indicator tag that is made from a fabric dyed with at least one dye to impart to the piece of fabric a predetermined initial color which indicates that the chemical treatment agent on the textile article is effective. The dye has a chromophore which is susceptible to degradation by reagents which would destroy the effectiveness of the chemical treatment agent so that exposure of the indicator tag to such reagents causes the indicator tag to change from its predetermined initial color to another color, thereby indicating a loss in the effectiveness of the protective chemical treatment agent on the textile article.

PCT publication no. WO 01/54661 published on Aug. 2, 2001 discloses a 2 layer cleansing article with therapeutic benefit components disposed adjacent to one layer of the article in a specified concentration and distribution pattern (FIGS. 6 and 7) and isolated by a reservoir seal from the remainder of the article. However there is no disclosure or suggestion of the effect of carrier solvent on therapeutic agent bleeding in the article to adjacent zones where no reservoir seal is used.

U.S. Pat. No. 6,231,719 to Garvey et al. issued on May 15, 2001 discloses a tissue product coated with a skin moisturizing formula in a stripewise pattern wherein the concentration of the skin moisturizing agent varies between the adjacent stripes. The skin moisturizing formula is a solid at room temperature and is coated onto the tissue product at elevated temperatures as a liquid melt. The skin moisturizing formula later solidifies onto the surface of the tissue.

Surprisingly, it has been found that wiping articles may be produced that contain a pattern of active zones containing one or more benefit agents selected from nondetergent active agents, conditioning agents, aesthetic agents or a mixture thereof for treating the skin or hair and further containing a critical range of carrier solvent sufficient to facilitate the transfer of the abovementioned agents from the active zone to the user when the article is wetted with water but below a level causing bleeding across the article interface of the agent(s) into adjacent non-active zones in the wiping article. It is a feature of the inventive wipe that the effective diffusion rate of the carrier solvent across the wipe article interface into the adjacent non-active zone is substantially identical to its diffusion rate adjacent to the interface, or in other words within the active zone. This is in contrast to prior art wiping articles that have liquid or moisture barriers separating the active zones from the non-active zones. It is another feature of the present invention that the coating composition containing the benefit agent is flowable at room temperature prior to any drying or removal of excess carrier solvent. Advantageously the coating composition has a melting point below 30 C. Optionally the active zone may contain a visual indicator associated with the benefit agent(s) whereby the disappearance or transformation of the indicator would signify the transfer of the benefit agent to the user. In another embodiment of the inventive wipe, specific active materials may be used as benefit agents that are either 1) unstable in a specific solvent mixture, such as vitamin C in an aqueous medium, or 2) are not compatible with other ingredients in a mixture such as salicylic acid with a surfactant, and the like. These agents may be separately coated onto the wiping article with a carrier solvent that does not degrade the specific active material or in a compatible blend of carrier solvent and other ingredients as the case may be. In this regard, a sufficient quantity of carrier solvent is used to solvate or disperse the active material so that the material will be rapidly released when the article is wetted with water and transferred to the skin or hair of the user. Advantageoulsy, the fact that the coating composition is a liquid at room temperature that does not require heating during the coating process is useful in incorporating heat labile benefit agents in the inventive article. The bleed resistant properties between adjacent active and non-active zones of the inventive wiping articles is conveniently expressed as the Dynamic Active Zone Depletion percentage described below.

SUMMARY OF THE INVENTION

In one aspect this invention relates to a disposable, single use personal care article, comprising:
a. a water insoluble substrate having an active zone, a non-active zone adjacent to the active zone, and an interface therebetween;
b. a coating composition with a melting point below 30 C, the coating composition containing at least one benefit agent selected from an active agent, a conditioning agent, an aesthetic agent and a mixture thereof for treating the skin or hair, the coating composition being releasably associated with the active zone;
c. a carrier solvent with an effective diffusion rate within the water insoluble substrate, the carrier solvent being selected from water, a water miscible compound, an oil, an oil soluble compound, and a mixture thereof; wherein the coating composition is dissolved, dispersed, or emulsified in the carrier solvent; and
d. wherein the effective diffusion rate of the carrier solvent across the interface is substantially identical to the diffusion rate of the carrier solvent adjacent to the interface.

In another aspect this invention relates to a method of manufacturing a disposable, single use personal care article, comprising the steps of:
a. preparing a composition including at least one benefit agent selected from an active agent, a conditioning agent, and an aesthetic agent;
b. adding in any sequence to the composition in (a) a lathering surfactant, a carrier solvent, and a visual indicator;
c. applying the composition prepared in (b) to in a pattern to a hydrophilic substrate using a method selected from coating, spraying, splashing, dipping, slot die coating, and stencil coating; and
d. adjusting in any sequence the water content of the article in the concentration range of about 5 to about 50% by weight based on the substrate; wherein the hydrophilic substrate containing the visual indicator contains less than about 20% of the lathering surfactant based on the substrate in the patterned area.

In a further aspect this invention relates to a method of depositing a benefit agent onto the skin or hair comprising the steps of:
a. providing an article composed of
 1. a water insoluble substrate having an active zone and a nonactive zone adjacent to the active zone;
 2. the active zone releasably containing the benefit agent, the benefit agent being selected from an active agent, conditioning agent, and aesthetic agent or a mixture thereof for treating the skin or hair; and
 3. at least one water-soluble or water dispersible visual indicator in contact with the benefit agent in the active zone in an amount sufficient to impart a distinct outward appearance to the active zone, the outward appearance being selected from a color dominant wavelength, color or shade density, and surface reflectivity whereby the outward appearance will vary indicating the transfer of the benefit agent to the user's skin or hair when the article is exposed to water;
(b) wetting the article with water; and applying the article to the skin or hair whereby the benefit agent is deposited thereon at a level between about 0.01 $\mu g/cm^2$ to about 20 $\mu g/cm^2$.

DETAILED DESCRIPTION OF THE INVENTION

Definitions:

the active zone coating weight/active zone substrate weight ratio:

$$\frac{\text{(weight of coating in active zone)}}{\text{(weight of substrate in active zone)}} =$$

$$\frac{\text{(weight of coating in active zone)}}{\text{(area of active zone)(basis weight of substrate)}}$$

the total cloth coating/total cloth substrate ratio:

$$\frac{\text{(weight of coating on entire article)}}{\text{(weight of substrate in entire article)}} =$$

$$\frac{\text{(weight of coating on entire substrate)}}{\text{(area of substrate)(basis weight of substrate)}}$$

Active Zone

A patterned area of the article that contains benefit agents that are dispersed uniformly throughout the patterned area on the cloth.

Non-Active Zone

A patterned area of the article that is adjacent to the Active zone and contains a lower concentration of benefit agents compared to the Active zone, preferably no benefit agents.

Distinct Outward Appearance

Distinct outward appearance is here defined as what the average observer would perceive under average illuminating conditions as described in e.g. ASTM and CIE standard test methods E308-01, E903-96, and the like for color, shade, and reflectance measurement.

Effective Diffusion Rate

The rate that the coating composition will diffuse within the water insoluble substrate during and after the coating process.

Figure 1:
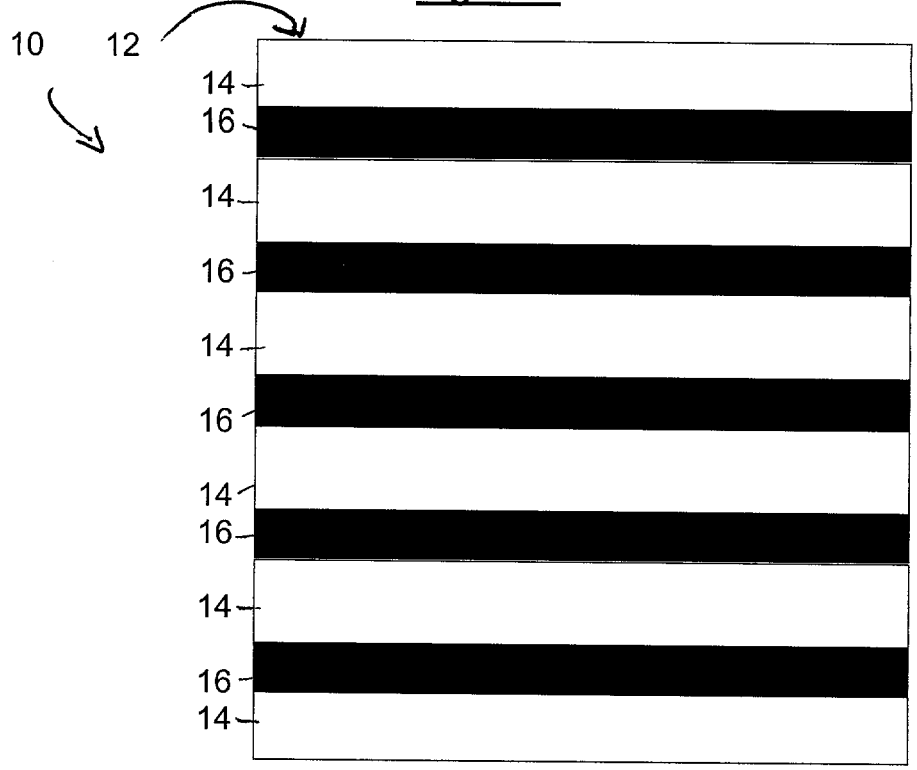
FIG. 1 is a top planar view of a cleansing article representing an embodiment of this invention containing a stripewise pattern of alternating active and non-active zones.
Figure 2:
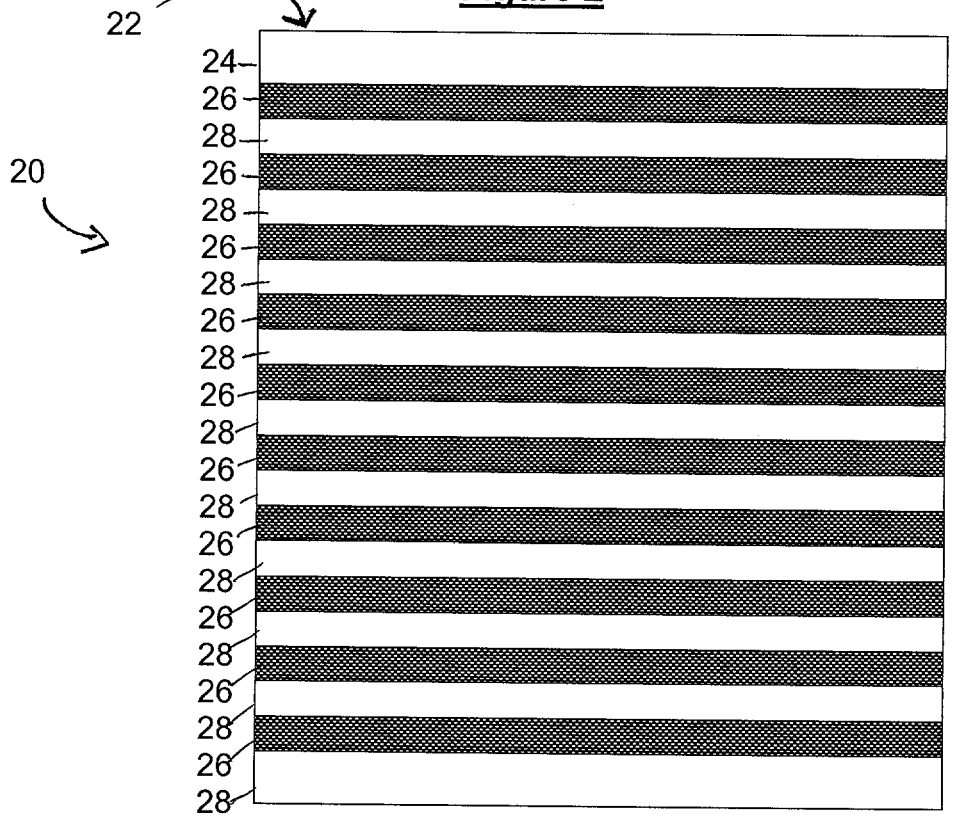
FIG. 2 is a top planar view of a cleansing article representing another embodiment of this invention containing a stripewise pattern of alternating active and non-active zones.
Figure 3:
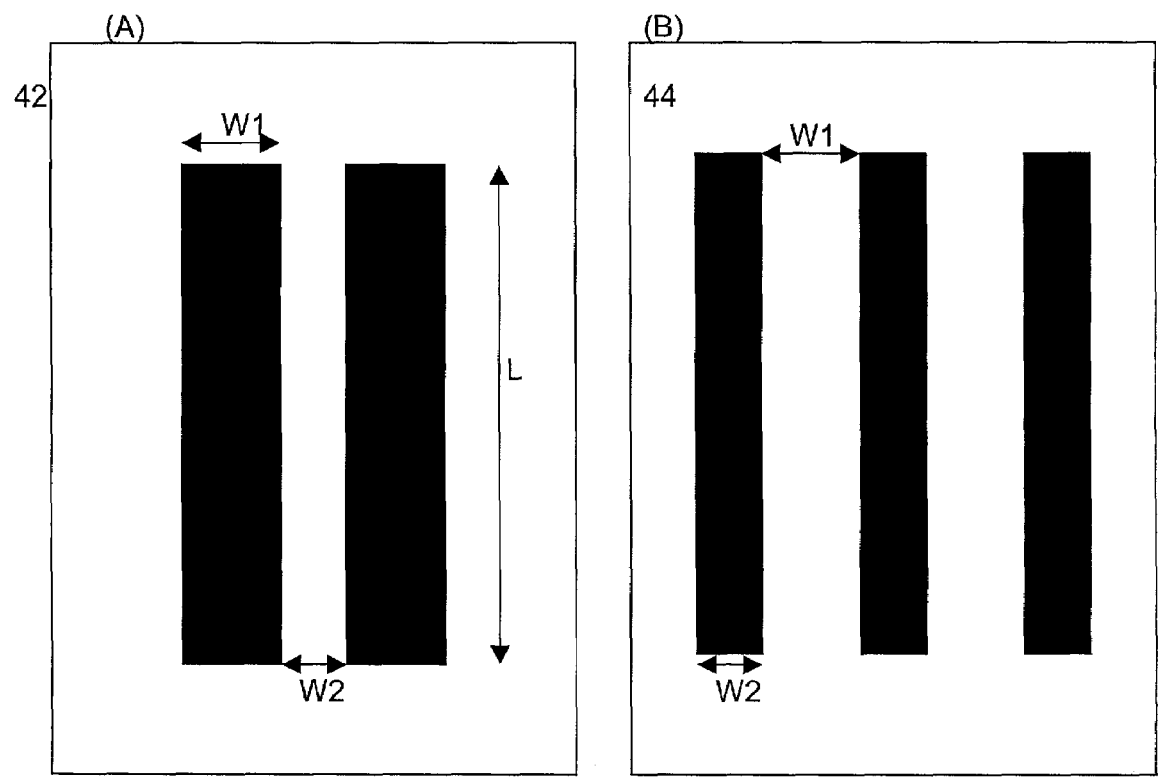
FIGS. 3A and B are top planar views of slot coating dies used to deposit a stripewise pattern of active and non-active zones respectively in another embodiment of this invention.
Figure 4:
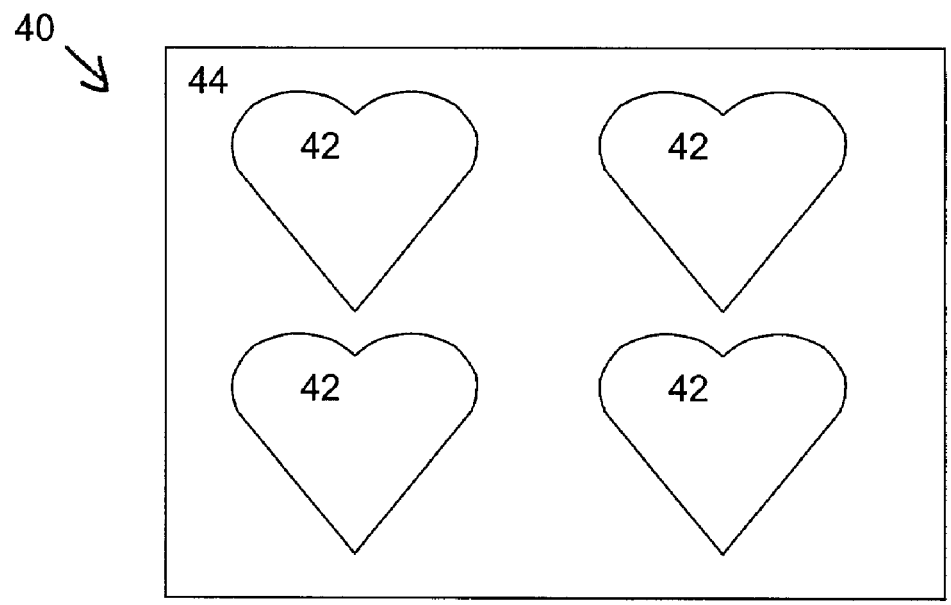
FIG. 4 is a top planar view of a cleansing article representing another embodiment of this invention containing a pattern of heart-shaped active zones surrounded by a non-active zone.

Referring now to the drawings in which like figures represent like elements, in FIG. 1, cleansing article 10 is made up of a water insoluble substrate or fabric 12 that is 153 mm wide and 190 mm long. Fabric 12 contains edge stripes 14, and alternating stripes 16 and 18 wherein stripes 16 contain a combination of benefit agent, a carrier solvent, a color dye indicator, and optionally a lathering surfactant, and stripes 18 contain a personal care composition that contains a lower concentration of benefit agent or color dye indicator, preferably no benefit agent or color dye indicator, then stripe 16. In this embodiment, stripe 14 is 15 mm wide, stripe 16 is 11 mm wide, and stripe 18 is 17 mm wide. In FIG. 2, cleansing article 20 is made up of a water insoluble substrate or fabric 22 that is 153 mm wide and 190 mm long. Fabric 22 contains edge stripes 24, and alternating stripes 26 and 28 wherein stripes 26 contain a combination of benefit agent, a carrier solvent, a color dye indicator, optionally a lathering surfactant; and stripes 28 contain a personal care composition that does not contain a benefit agent, or color dye indicator. In this embodiment, stripe 24 is 10 mm wide, and stripes 26 and stripes 28 both are 7 mm wide. In FIG. 3, slot coating dies A and B are used to deposit a stripewise pattern of active zones 42 and non-active zones 44 respectively on a substrate in another embodiment of this invention. Active zones 42 are 7.5 inches long (L) and 1.5 inches wide (w1). Non-active zones 44 are 7.5 inches long (L) and 1.0 inch wide (w2). Now referring to FIG. 4, cleansing article 40 is made up of a water insoluble substrate or fabric 46 containing active zones 42 and non-active zone 44. Active zones 42 all contain a combination of benefit agenta carrier solvent, a color dye indicator, optionally a lathering surfactant; and non-active zone 44 contains a personal care composition that does not contain a benefit agent, or color dye indicator.

In one aspect of the invention is a disposable, single use personal care article, comprising:
(a) a water insoluble substrate having an active zone, a non-active zone adjacent to the active zone, and an interface therebetween;
(b) a coating composition with a melting point below 30 C, the coating composition containing at least one benefit agent selected from an active agent, a conditioning agent, an aesthetic agent and a mixture thereof for treating the skin or hair, the coating composition being releasably associated with the active zone;
(c) a carrier solvent with an effective diffusion rate within the water insoluble substrate, the carrier solvent being selected from water, a water miscible compound, an oil, an oil soluble compound, and a mixture thereof; wherein the coating composition is dissolved, dispersed, or emulsified in the carrier solvent; and
(d) wherein the effective diffusion rate of the carrier solvent across the interface is substantially identical to the diffusion rate of the carrier solvent adjacent to the interface.

Advantageously, the active zone contains a higher total benefit agent concentration then the non-active zone based on the weight of the substrate. Preferably the benefit agent in the active zone is in the concentration range of about 0.01% to about 100% by weight; or about 0.05 to 50% by weight; more preferably about 0.5 to 20% by weight based on the substrate.

Advantageously, the dynamic active zone depletion percentage of the benefit agent is less than about 50%, 30%, 25%, 20%, 10%, or 5% based on the weight of the substrate.

Preferably the water insoluble substrate comprises at least one layer of a woven or non-woven fabric and the benefit agent is deposited in a pattern on the fabric. Most preferably the substrate comprises a plurality of layers and the benefit agent is coated onto at least one layer of a portion of the water insoluble substrate.

Advantageously, the total coating weight in the active zone is in the concentration range of about 1% to about 400% by weight, preferably about 5% to 200%; most preferably about 30% to 150% by weight based on the substrate. Preferably the personal care article has at least one lathering surfactant contained in the non-active zone. More preferably the lathering surfactant is in the concentration range of about 2% to about 100%; preferably about 5 to 50% by wt. based on the substrate and the active zone contains less than about 20%, 10%, 5%, 1%, 0.5%, or 0.1 wt. % by wt. of a lathering surfactant and most preferably the active zone contains no lathering surfactant.

With respect to the carrier solvent in the active or non-active zone, the solvent is advantageously in a concentration range of about 5 to about 160 wt. %; preferably about 10 to 160 wt. %; and more preferably about 10 to 100 wt. %; based on the substrate. Below the level of 5% the transfer of the benefit agent is slow and disadvantageous to the user of the personal care article. Above the level of 160% by wt. the tendency for the active and adjacent zones to bleed into one another is unacceptable. The carrier solvent preferably includes a compound selected from water, a polyhydric alcohol, a polyol, and a blend thereof; and the like. Most preferably the carrier solvent contains at least about 20% by weight of water.

Advantageously, the ratio of carrier solvent to article absorptive capacity in the active or non-active zone is below about 0.13, 0.12, 0.11, or 0.10. Preferably at least one layer of the woven or non-woven fabric comprises a hydrophilic fabric. More preferably the hydrophilic fabric is a blend of cellulosic and non-cellulosic fibers. Most preferably the hydrophilic fabric comprises rayon and polyester. The hydrophilic fabric may further comprise rayon and polyester in the concentration ratio range of about 9.8 to 1.0; preferably about 7 to 3. Most preferably the hydrophilic fabric contains a plurality of apertures having a major (or long) axis diameter in the range of about 0.5 to about 10 mm and wherein the apertures are distributed on the substrate in the range of about 1 to about 10 per linear centimeter. Still more preferably the hydrophilic fabric includes at least one layer of fibers made by a process selected from hydroentangled, wet laid, dry laid, spun bonded, needle punched, and air laid.

In another respect, the inventive personal care article preferably has a concentration ratio of the sum of benefit agents and lathering surfactant to the substrate of less than about 5.0 based on the weight of the substrate.

The inventive personal care article may contain at least one active agent selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; and a mixture thereof; and the like.

Preferably the personal care further includes at least one water-soluble or water dispersible indicator in contact with the benefit agent in the active zone of the substrate in an amount sufficient to impart a distinct outward appearance to the active zone which differs from the adjacent zone, the outward appearance being selected from a color dominant wavelength, color or shade density, and surface reflectivity, and whereby the outward appearance of the active zone will vary indicating the transfer of the benefit agent to the user's skin or hair when the article is exposed to water. Advantageously, the indicator is a cosmetically suitable dye that either is at least partially solvated, dispersed, or suspended in the carrier solvent or that is substantively bonded to the water insoluble substrate. Preferably the indicator is selected from a permanent dye; a pH sensitive dye; an encapsulated dye adjacent to a barrier layer; a leuco dye; and a dye substantively bonded to the active agent, conditioning agent, or aesthetic agent. In the case where an encapsulated dye is employed, it may be released by mechanical rupture, dissolution, or permeation of the barrier layer by a substance selected from water, active agents, conditioning agents, aesthetic agents, lathering surfactants, water miscible solvents, oils, oil soluble solvents, or a mixture thereof; and the like.

Advantageously, the inventive personal care article's active zone has a distinct pattern selected from stripes, geometric shapes, amorphous shapes, symbols, indicia and a combination thereof; and the like. In one respect the active zone and the adjacent zone may be oriented as stripes with substantially parallel boundary lines.

In another embodiment is a method of manufacturing a disposable, single use personal care article, including the steps of:

(a) preparing a composition including at least one benefit agent selected from an active agent, a conditioning agent, and an aesthetic agent;

(b) adding in any sequence to the composition in (a) a lathering surfactant, a carrier solvent, and a visual indicator;

(c) applying the composition prepared in (b) to in a pattern to a hydrophilic substrate using a method selected from coating, spraying, splashing, dipping, slot die coating, and stencil coating; and (d) adjusting in any sequence the water content of the article in the concentration range of about 5 to about 50% by weight based on the substrate; wherein the hydrophilic substrate containing the visual indicator contains less than about 20% of the lathering surfactant based on the substrate in the patterned area.

In a further embodiment is a method of depositing a benefit agent onto the skin or hair including the steps of:

(a) providing an article composed of
  i) a water insoluble substrate having an active zone and a nonactive zone adjacent to the active zone;
  ii) the active zone releasably containing the benefit agent, the benefit agent being selected from an active agent, conditioning agent, and aesthetic agent or a mixture thereof for treating the skin or hair; and
  iii) at least one water-soluble or water dispersible visual indicator in contact with the benefit agent in the active zone in an amount sufficient to impart a distinct outward appearance to the active zone, the outward appearance being selected from a color dominant wavelength, color or shade density, and surface reflectivity whereby the outward appearance will vary indicating the transfer of the benefit agent to the user's skin or hair when the article is exposed to water;

b) wetting the article with water; and c) applying the article to the skin or hair whereby the benefit agent is deposited thereon at a level between about 0.01 µg/cm$^2$ to about 20 µg/cm$^2$.

Water Insoluble Substrate:

The inventive personal care article contains a water insoluble substrate as a component. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include The substrate may for example be a woven or nonwoven fabric, paper, tissue, sponge or laminate of foam and fabric. Examples of suitable nonwoven substrates would be wet-laid, dry-laid, spun bonded, hydroentangled, air-laid, and the like comprising either singly or in admixture fibers such as cellulose, rayon, polyester, polypropylene, polyethylene, polyamide, and the like. The term substrate also includes naturally occurring materials such as animal skin e.g. chamois leathers and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful as components in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Non-limiting examples of synthetic materials useful as components in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like; polyesters such as Fortrel®, Kodel®, and the polyethylene terephthalate fibers, Dacron®); polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers. Substrates made from natural materials useful in the present invention can be obtained from a wide variety of commercial sources.

Non-woven substrates made from synthetic material useful in the present invention can also be obtained from a wide variety of commercial sources, such as e.g. Sontaro® 8868, a hydro-entangled material, containing about 50% cellulose and about 50% polyester, and having a basis weight of about 60 gsy or 2.2 oz per sq. yard, having rectangular apertures of about 1.5 mm by 2 mm in dimension with about 150 to 160 apertures per sq. inch, available from Dupont Chemical Corp; PGI Laveft fabric, a 2.35 oz/sq. yd., 63% rayon/29% PET/8% binder fabric with rectangular apertures of about 2 mm×3 mm in dimension having about 40 to 45 apertures per square inch from PGI Corporation; Carlee high loft fabric, 2.0 oz/sq.yd., 100% polyester fabric from Carlee Corporation; and KC 5A high loft fabric, approx. 2.5 oz per sq. yard, 100% polyester fabric from Kimberly Clark Corporation.

Most preferred as a component substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

Anywhere from 1 to 100, preferably from 5 to 50 single wipe articles may be stored within a dispensing pouch or container, preferably a moisture impermeable pouch or container. During storage and between dispensing, the pouch or container is preferably resealable. Single wipe containing pouches may also be employed.

Apertured Fabrics

The inventive cleansing article may optionally include at least one apertured fabric, where a pattern is created by a network of bundled fiber segments surrounding apertures or holes; or in a contiguous nonwoven web which has been apertured or provided with slits or other openings. In one preferred embodiment, the water insoluble matterial is a substantially contiguous network of water insoluble fibers having a plurality of macroscopic openings. A macroscopic opening is defined as an opening that is large relative to the intrinsic pore size of the water insoluble material.

In a typical spunbond or bonded carded web, for example, a macroscopic opening would appear to the eye to be a deliberately introduced hole or void in the web rather than a characteristic pore between adjacent fibers, and specifically could have a characteristic width or major axis diameter of about 0.1 mm to about 10 mm, or larger; preferably about 1 mm to about 5 mm. A useful characteristic width may be defined as 4 times the area of the aperture divided by the perimeter. Useful fabric aperture densities are about 10 to 700 per square inch, preferably about 20 to 500 per square inch.

As discussed above, the nonwoven web may be made from synthetic fibers, as is known in the art, and may be a spunbond web, a meltblown web, a bonded carded web, or other fibrous nonwoven structures known in the art. For example, a polyester nonwoven web such as a low basis weight spunbond material could be provided with apertures through pin aperturing; perf embossing and mechanical stretching of the web; die punching or stamping to provide apertures or holes in the web; hydroentangling to impart apertures by rearrangement of the fibers due to the interaction of water jets with the fibrous web as it resides on a patterned, textured or three-dimensional substrate that imparts a pattern to the web; water knives that cut out desired apertures or holes in the web; laser cutters that cut out portions of the web; patterned forming techniques, such as air laying of synthetic fibers on a patterned substrate to impart macroscopic openings; needle punching with sets of barbed needles to engage and displace fibers; and other methods known in the art. Preferably, the openings are provided in a regular pattern over at least a portion of an outersheet of the absorbent article.

The water insoluble substrates or fabrics of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different permanent colors as distinguished from the variable indicator contained in the article, thereby helping the user to further distinguish the surfaces.

The apertured fabric or sheet may be bonded to at least one other nonwoven sheet of water insoluble fibers ("second sheet") by lamination, adhesives, stitching, fasteners, or other art recognized binding methods. Preferably, the second sheet is attached to the apertured sheet by means of lamination, adhesives and related agents, including hot melts, latexes, glues, starch, waxes, and the like, which adhere or join the upper regions of the apertured sheet with adjacent portions of the second sheet. Preferably, adhesives are applied only to the most elevated portions of the apertured sheet to effect the bonding between the apertured sheet and the second sheet, leaving the apertures substantially free of adhesive. Adhesive application can be through meltblown application of hot melt glues and thermoplastic materials, spray or swirl nozzles of melted or dissolved adhesives, printing of adhesive material onto one or both surfaces before joining, and the like. If adhesives are applied directly to the apertured sheet by means of spray, mist, aerosol, or droplets in any form, prior to contact of the apertured sheet with the water insoluble matter, then it is desirable to use a template or patterned shield to prevent application of adhesive to the apertures to avoid clogging. Preferably, the second sheet is composed of polyester or a polyester and cellulose blend, does not contain apertures and has the characteristics of high loft, a basis weight of about 1 to 5 ounces per square yard, preferably about 2 to 3 ounces per square yard and optionally contains a binder. Useful binders include latex or acrylic materials added to the fabric between about 5 to 40 weight percent of the fabrics total weight, preferably between about 5 to 25 weight percent.

Benefit Agents:

1) Active Agents

The personal cleansing articles of the present invention may contain a safe and effective amount of an active agent as a benefit agent in the active zone. This active agent may be selected from water soluble active agents, oil soluble active agents, pharmaceutically-acceptable salts and mixtures thereof. The term "active agent" as used herein, means personal care actives which can be used to deliver a benefit to the skin and/or hair and which generally are not used to confer a conditioning benefit, as hereinafter defined. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the articles of the present invention comprise from about 0. 01% to about 50%, more preferably from about 0.05% to about 25%, even more preferably 0.1% to about 10%, and most preferably 0.1% % to about 5%, by weight of the substrate, of the active agent component.

A wide variety of active agent ingredients are useful herein and include those selected from anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, anti-glycation actives and mixtures thereof and the like.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids and bioflavonoids; bile salts such as scymnol sulfate and its derivatives, deoxycholate, and cholate.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentarnidine, gentamicin, kanamycin, lineomycin, methacycline, methenamine, minocycline, neomycin, netilmicin, paromomycin, streptomycin, tobramycin, miconazole, and tetracycline hydrochloride, erythromycin, zinc erythromycin, erythromycin estolate, erythromycin stearate, amikacin sulfate, doxycycline hydrochloride, capreomycin sulfate, benzalkonium chloride; benzethonium chloride; benzoic acid and its salts; triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), salicylic acid and derivatives thereof (such as 5-octanoyl salicylic acid, heptyloxy 4 salicylic acid, and 4-methoxy salicylic acid); sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid; skin peel agents (e.g., phenol), mixtures thereof, and the like.

Skin barrier repair actives are those skin care actives which can help repair and replenish the natural moisture barrier function of the epidermis. Nonlimiting examples of skin barrier repair actives include Alpha Lipid (available from Lucas Meyer); ascorbic acid; biotin; biotin esters; brassicasterol; caffeine; campesterol; canola derived sterols; Cennamides (available from Ennagram); Ceramax (available from Alban Muller); CERAMAX (available from Quest, located in Ashford, England); Ceramide derivatives; mixtures thereof, and the like.

Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; biphenylcarboxylic acid derivatives; oxicams, mixtures thereof, and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; acetyl tyrosine; phospho-DOPA; brazilin; caffeine; coffee extracts; dihydroxyacetone; DNA fragments; isobutyl methyl xanthine; methyl xanthine; Phototan (available from Laboratoires Serobiologiques); prostaglandins; tea extracts; theophylline; tyrosine; UNIPERTAN P2002 and UNIPERTAN P27 (both available from Unichem); mixtures thereof, and the like.

Skin lightening actives can actually decrease the amount of melanin in the skin or provide an such an effect by other mechanisms. Nonlimiting examples of skin lightening actives useful herein include aloe extract, alpha-glyceryl-L-ascorbic acid, aminotyroxine, ammonium lactate, anethole derivatives, butyl hydroxy anisole, butyl hydroxy toluene, butyl resourcinol, ellagic acid, gluconic acid, glucosamine, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminium hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates. Other suitable skin tightening agents include Biocare SA (available from Amerchol); egg albumen; Flexan 130 (available from National Starch); Gatuline Lifting (available from Gattefosse); Pentacare HP (available from Pentapharm); Vegeseryl (available from Laboratories Serobioloques) and mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspastic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Preferred examples of actives useful herein include those selected from salicylic acid, benzoyl peroxide, 3-hydroxy benzoic acid, glycolic acid, lactic acid, 4-hydroxy benzoic acid, acetyl salicylic acid, niacinamide, cis-retinoic acid, trans-retinoic acid, retinol, retinyl palmitate, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, 2-ethylhexyl p-methoxycinnamic acid, oxybenzone, 2-phenylbenzimidozole-5-sulfonic acid, dihydroxyacetone, panthenol, lactic acid, arbutin, kojic acid, allantoin, cholesterol, C 10-C 30 cholesterol/lanosterol esters, tocopherol, tocopheryl acetate, and mixtures thereof.

2) Conditioning Agents

Skin conditioning agents also known as emollients may be advantageously used in the present invention as benefit agents. The emollient "composition" may be a single agent component or it may be a mixture of two or more compounds one or all of which may have a conditioning aspect. In addition, the conditioning agent itself may act as a carrier for other components one may wish to add to the personal care article.

Hydrophobic emollients, hydrophilic emollients, or a blend thereof may be used. Hydrophobic emollients are preferably present in a concentration greater than about 5% by weight of the coating composition contained in the active zone of the water insoluble substrate, more preferably greater than about 10% by weight based on the weight of the substrate. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils. Silicones of a volatile and non-volatile variety are included. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source.

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline®), microcrystalline wax, ceresin, squalene, pristan and mineral oil;

(f) higher alcohols such as lauryl, cetyl, stearyl, oleyl, behenyl, cholesterol and 2-hexydecanol alcohol;

(g) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(h) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(i) lipids such as cholesterol, ceramides, sucrose esters and pseudo-ceramides as described in European Patent Specification No. 556,957 incorporated herein by reference;

(j) vitamins, minerals, and skin nutrients such as milk, vitamins A, E, and K; vitamin alkyl esters, including vitamin C alkyl esters; magnesium, calcium, copper, zinc and other metallic components;

(k) sunscreens such as octyl methoxyl cinnamate (Parsol MCX) and butyl methoxy benzoylmethane (Parsol 1789);

(l) phospholipids;

(m) antiaging compounds such as alpha hydroxy acids, beta hydroxy acids; and (n) mixtures of any of the foregoing components, and the like.

Preferred emollient benefit agents are selected from triglyceride oils, mineral oils, petrolatum, and mixtures thereof. Especially preferred are triglyceride oils.

3) Aesthetic Agents

Aesthetic agents either alone or in combination may be advantageously used in the present invention as benefit agents. Useful aesthetic agents include fragrances, colorants, cosmetics, and the like. Warming components such as zeolites, magnesium chloride, water collapsable beads, and the like may also advantageously be included.

Water Soluble/Dispersible Dyes

Certified dyes that are suitable as visual indicators for the inventive wipe are synthetic organic coal tar derivatives which are manufactured so that each batch passes a Food & Drug Administration (FDA) purity inspection. If approved by the FDA, these dyes are certified for use in foods, drugs, cosmetics (FDC colors), drugs and foods only (DC colors), or in topically applied drugs and cosmetics (External DC colors). Certified dyes can be water soluble or lakes. Lakes are organic pigments prepared by precipitating a soluble dye on a reactive or absorbent stratum which is an essential part of the pigment's composition. Most lakes are aluminum, barium or calcium derived. These insoluble pigments are used mostly in makeup products, either powders or liquids, when a temporary color is desired that won't stain the skin (as oil-soluble dyes tend to do). The lakes are used in these products along with inorganic colors such as iron oxide, zinc oxide and titanium dioxide.

These colorants can be added to either isotropic systems or into emulsions. When incorporating these dyes in an emulsion, they will be soluble in the external water phase in an oil/water system. It is useful to know the solubility properties of the certified dyes in various solvents and their stability to reactive chemicals in order to make a stable coating compositon. Table A lists some of the currently available water soluble certified dyes.

TABLE A

WATER-SOLUBLE DYES

FDC Blue #1
FDC Blue #2
FDC Green #3
FDC Red #3
FDC Red #4
FDC Yellow #5
FDC Yellow #6
DC Green #5
DC Red #22
DC Red #28
DC Red #33
DC Yellow #10
Ext DC Violet #2
Ext DC Yellow #7
DC Green #8
DC Orange #4
DC Yellow #8

When using these dyes in an emulsion or isotropic system, they can be added drop by drop from a prepared solution to obtain or to match a particular shade. Or the dyes can be premixed to a certain color and then added to the coating composition.

The coating composition should contain the water-soluble color dye (visual indicator) in an amount sufficient to enable the coating composition to be readily visualized (i.e. colored) when applied to the active zone of the water insoluble substrate. One or more water-soluble or dispersible dyes can be employed in the composition in an amount ranging from about 0.0005 to about 0.5% by weight of the coating composition, preferably from about 0.002 to about 0.2%, more preferably from about 0.01 to about 0.05%, and most preferably from about 0.02 to about 0.04%.

Lathering Surfactant

The inventive personal care article optionally contains a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically comprise a lathering surfactant in a concentration of about 0.0% to about 500%, preferably between about 1% to about 200%, more preferably from about 5% to about 40% based on the weight of the substrate containing the surfactant.

A wide variety of lathering surfactants are useful herein and include those selected from anionic, nonionic, cationic, amphoteric and lathering surfactants, mixtures thereof, and the like.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3^-M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$-$C_{16}$ olefin sulfonate, available as Bioterge AS 40®

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as e.g. Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3^-M^+)CO_2R^2$ where $R^1$ is straight or branched alkyl from about $C_8$- to $C_{18}$, preferably $C_{12}$ to $C_{16}$, an $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 18 carbon atoms, with sodium lauryl lactylate sold as Pationic 138 C® available from the Patterson Chemical Company as the most preferred.

(13) Taurates having from 8 to 16 carbon atoms, with cocoyl methyl taurate being preferred.

Nonionic lathering surfactants suitable for the present invention include $C_{10}$-$C_{20}$ fatty alcohol or acid hydrophobes condensed with from 2 to 100 moles of ethylene oxide or propylene oxide per mole of hydrophobe; $C_2$-$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$-$C_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethylododecylamine oxide, oleyidi(2-hydroxyethyl)amine oxide, dimethyloctylamine oxide, dimethyidecylamine oxide, dimethyltetradecylamine oxide, di(20-hydroxyethyl)tetradecylamine oxide, 3-didodecyoxy-2-hydroxypropyidi(3-hydroxypropyl)amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocoamidopropyl betaine, cocoamphoacetate, cocoamphodiacetate, cocoamphopropionate, cocoamphodipropionate, cocoamidopropyl hydroxysultaine, cetyl dimethyl betaine, cocoamidopropyl PG-dimonium chloride phosphate, coco dimethyl carboxymethyl betaine, cetyl dimethyl betaine and combinations thereof.

Carrier Solvent

The inventive article contains a carrier solvent that is associated with a surfactant and/or the active zone benefit components i.e. active agent, conditioning agent, aesthetic benefit agent, and that is present in a concentration sufficient to preactivate the surfactant or active zone components so that they are readily transferred to the user when the article is wetted with water. Suitable carrier solvents include water, water miscible solvents such as alcohols, polyols, and polyhydric alcohols; and the like; and oils and oil miscible solvents such as triglyceride oils, mineral oils, silicone oils and the like. Suitable examples of water miscible solvents include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, ethoxylated glycerol, propoxylated glycerol and mixtures thereof. The most preferred is water, glycerin, and propylene glycol. Suitable examples of oils and oil miscible solvents include mineral oil, vegetable oil, and silicone oil.

Amounts of the carrier solvent may range from about 0.5% to about 160%, preferably from about 1% to about 160%, and more preferably from about 2% to about 100%, by weight based on the substrate.

Suitable silicone oils may be of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01% to about 100%, preferably from about 1% to about 10% by weight of the substrate.

Skin Feel Agents

The inventive article may also optionally contain skin feel agents. Suitable agents include cationic conditioning agents in monomeric and polymeric type. Examples of the polymeric type include: cationic cellulose derivatives, cationic starches, copolymers of a diallyl quaternary ammonium salt and an acryl amide, quaternized vinylpyrrolidone, vinylimidazole polymers, polyglycol amine condensates, quaternized collagen polypeptide, polyethylene imine, cationized silicone polymer (e.g. Amodimethicone), cationic silicone polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16 etc. manufactured by the Celanese Company), quaternary ammonium salt polymers (e.g. Mirapol A-15, Mirapol AD-1, Mirapol AZ-1, etc., manufactured by the Miranol Division of the Rhone Poulenc Company). Most preferred is polyquaternium 10, amodimaethicone, and catonized guar gum.

Examples of monomeric cationic conditioning agents are salts of the general structure:

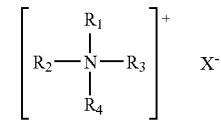

Wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carbon atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicone quats may similarly be employed. Most preferred is Silquat AD designated by the CTFA as Silicone Quaternium 8, available from Siltech Inc.

Amounts of each cationic agent may range from about 0.001% to about 10% preferably from about 0.01% to about 5%, optimally from about 0.1% to about 2% by weight of the substrate.

Manufacturing Methods

The disposable, single use personal care products of the present invention are manufactured by separately or simultaneously adding onto or impregnating into a water insoluble substrate a skin active agent, conditioning agent or aesthetic benefit agent, carrier solvent, indicator and optionally a lathering surfactant. By "separately" is meant that the components can be added sequentially, in any order without first being combined together. By "simultaneously" is meant that the components can be added at the same time, with or without first being combined together.

The components and any optional ingredients can be added onto or impregnated into the water insoluble substrate by any means known to those skilled in the art. For example, addition can be through spraying, printing, splashing, dipping, soaking, or coating, flood coating, spray coating or metered dosing. More specialized techniques, such as Meyer Rod, floating knife or doctor blade may also be used herein.

When water is used as a carrier solvent or present in the manufacturing process, the resulting treated substrate may then dried sufficiently to attain the desired carrier solvent level. The treated substrate can be dried by any means known to those skilled in the art. Non-limiting examples of known drying means include the use of convection ovens, radiant heat sources, microwave ovens, forced air ovens, and heated rollers or cams. Drying also includes air drying without the addition of heat energy, other than that present in the ambient environment. Also, a combination of various drying methods can be used.

Prior to or after impregnation of the components into the wiping article, the article may be folded into stacks. The wiping article is then typically packaged in any of the moisture and vapor impermeable packages known in the art.

Method of Using the Treated Wipe Articles

For treatment of the user's skin or hair, the treated wipe is saturated with water, manipulated manually to generate a lather, and is applied to a surface (e.g., skin or hair surface) via topical application to release or deposit an effective amount of the aqueous liquid composition to perform the desired cleansing or other function. The amount of water-insoluble functional ingredient delivered from the wipe and frequency of topical application can vary widely, depending upon the individual user's needs. With respect to personal application to the skin, such application can range from about once per day to about four times daily, preferably from about twice per day to about three times daily. Number of wipes used per application can range from 1 to about 4 wipes, preferably 1 to about 2 wipes. The amount of skin active agent, conditioning agent or aesthetic benefit agent deposited on each wipe is generally from about 3.5 mg to about 175 mg per wipe. The treated wipes of the present invention can also be used prophylactically by administrating to healthy skin surfaces to guard from or prevent undesired skin conditions and/or infections using the dosing regimen described above.

Except in the operating and comparative examples, or where otherwise explicitly indicated, all numbers in this description indicating amounts of material ought to be understood as modified by the word "about".

The following nonlimiting examples will more fully illustrate the embodiments of this invention. All parts, percentages and proportions referred to herein and in the appended claims are by weight unless otherwise illustrated.

EXAMPLE 1

The effect of coating wt and carrier solvent concentration on interzone bleed on a 70/30 apertured rayon/polyester blend cloth (PGI Miratech miniherringbone pattern) with a basis weight of 65 gms/sq. meter and dimensions of 153 mm wide and 190 mm long was studied and the results are shown in table 1. This cloth had a 1:1 water/glycerin absorptivity of 1236%. Interzone coating bleed was visually assessed after coating the cloth and allowing the cloth to remain at 23 C in a sealed plastic bag for 20 hours. Coating and carrier solvent wt % is based on the substrate weight.

TABLE 1

| Cloth | Coating wt. % (non active zone) | Coating wt. (active zone) | Carrier solvent wt. % (non active zone) | Carrier solvent wt. (active zone) | Interzone Bleed Detected | Inventive (I)/ comparative (C) |
| --- | --- | --- | --- | --- | --- | --- |
| A | 157 | 15 | 127 | 12 | No | I |
| B | 83 | 147 | 67 | 118 | No | I |
| C | 83 | 441 | 67 | 350 | Yes | C |
| D | 8 | 147 | 6 | 118 | No | I |
| E | 66 | 176 | 53 | 141 | No | I |
| F | 67 | 147 | 54 | 118 | No | I |
| G | 83 | 147 | 67 | 118 | No | I |
| H | 83 | 147 | 67 | 118 | No | I |

Cloths A to E were slot die coated in an alternating striped pattern with solution I (table 4) for the non-active zone and solution 11 (table 5) for the active zone shown in FIG. 1 Cloth (F) was slot die coated in an alternating striped pattern shown in FIG. 2. Solution II contained a dye indicator to distinguish the active zone from the non-active zone in cloths A to E.

Cloths G and H were stencil coated with solution I (for the nonactive zone) and solutions III & IV (tables 6 and 7 respectively) for the active zones respectively in the alternating striped pattern shown in FIG. 1. Solutions I, III, and IV were formulated without a dye indicator.

Slot die coating was performed as follows: the coating solution is pumped onto the substrate or fabric through a die with a "slot" in it at a controlled rate. Typically the rate is adjusted to deposit the desired amount of coating onto the substrate. The rate will vary with the feed weight of the substrate to be coated. The slot is typically a thin opening that may expand the width of the fabric to be coated. In this example, the die contains 2 slots into which different coating solutions can be pumped. The colored coating solution, or coating solution with active, conditioning or aesthetic benefit agent, is pumped through one slot and the effluent is channeled so that a predetermined pattern defined by the slots, e.g. a striped pattern, is produced. The clear or uncolored coating solution (without the active, conditioning or aesthetic benefit agent), passes through another slot and its effluent is channeled so that the clear coating solution flows onto the substrate or fabric in another predetermined pattern, e.g. in locations not containing the colored solution or active agent, etc.

Stencil die coating was performed as follows: stencils were made of mylar film and the shaded areas represent where holes were cut out of the mylar (see e.g. FIGS. 1 and 2). The stencils were designed so that the open area of each stencil is approximately 22.5 in². First, the stencil used to put on the colored coating solution was placed over a 6"×7.5" cloth. Coating was then evenly applied over the entire open area (both sides of the substrate) at the desired level. A 0.5 in. wide, 1.0 inch long paintbrush was used. The brush was cleaned by directing a stream of warm water through the brush, with manual agitation, and a second stencil was used to apply the uncolored coating solution with a clean brush. The uncolored coating solution was then coated on the fabric at the desired level with care being taken that it be applied evenly over the area of all three openings. The finished cloths were then folded such that colored coating only came in contact with colored coating on the other side, and placed in two polyethylene plastic bags, sealed, and tested for interzone bleed stability.

EXAMPLE 2

The effect of the composition of the cloth and the viscosity of the coating solution on the stability of active zones to resist interzone bleeding was studied. Substrates composed of 70/30 and 10/90 rayon/polyester blend cloths and a 100% polyester cloth were compared. The cloths had the following water and 1:1 water/glycerin absorptivities (average of 5 measurements) as determined by INDA Association of the Nonwoven Fabrics Industry standard test method IST 10.1 (95):

| Cloth | Water absorptivity (%) | 1:1 water/glycerin absorptivitiy (%) |
|---|---|---|
| 70/30 rayon/polyester | 1173.5 | 1228.9 |
| 10/90 rayon/polyester | 1244.5 | 1235.7 |
| 100% polyester | 1172.2 | 1529.9 |

Cloths were stencil coated in an alternating stripewise pattern as illustrated in FIG. 3 with using coating solutions as described in tables below. Active zones and non-active zones had equal total coating and carrier solvent coating weight concentrations. The interzone bleed results, as measured by visual detection, are shown in table 2. Comparative cloths with carrier solvent coating weights in excess of 160 wt. % based on the substrate showed interzone bleed but inventive cloths with carrier solvent under 160% did not show interzone bleed for all cloth composition samples tested. The 160 wt % of carrier solvent observed limit corresond to an added solvent to maximum solvent absorptive capacity (for 1:1 water/glycerin) of about 0.13 for the 70/30 and 10/90 rayon/polyester blend cloths and about 0.10 for the polyester cloth. The ratio was caclulated as follows:

$$\text{Ratio} = \frac{\text{Added solvent as wt. \%}}{\text{Absorptive capacity as wt. \%}}$$

TABLE 2

| Cloth composition | Coating solution Non-Active zone | Coating solution Active zone | Coating weight % | Carrier solvent wt % | Coating solution viscosity (cps) | Interzone bleed detected | Inventive (I)/ Comparative (C) |
|---|---|---|---|---|---|---|---|
| 10/90 rayon polyester[1] | Table 12 | Table 13 | 100 | 81 | 290 | No | I |
| 10/90 rayon polyester[1] | Table 12 | Table 13 | 200 | 162 | 290 | Yes | C |
| 10/90 rayon polyester[1] | Table 14 | Table 15 | 100 | 81 | 1 | No | I |
| 10/90 rayon polyester[1] | Table 14 | Table 15 | 200 | 162 | 1 | Yes | C |
| 70/30 rayon polyester[2] | Table 12 | Table 13 | 100 | 81 | 290 | No | I |
| 70/30 rayon polyester[2] | Table 12 | Table 13 | 200 | 162 | 290 | Yes | C |
| 70/30 rayon polyester[2] | Table 14 | Table 15 | 100 | 81 | 1 | No | I |
| 70/30 rayon polyester[2] | Table 14 | Table 15 | 200 | 162 | 1 | Yes | C |
| 100% polyester[3] | Table 12 | Table 13 | 100 | 81 | 290 | No | I |
| 100% polyester[3] | Table 12 | Table 13 | 200 | 162 | 290 | Yes | C |
| 100% polyester[3] | Table 14 | Table 15 | 100 | 81 | 1 | No | I |
| 100% polyester[3] | Table 14 | Table 15 | 200 | 162 | 1 | Yes | C |

[1]PGI Miratech miniherringbone pattern
[2]PGI hydroentangled 7086
[3]PGI spunlaced M022

EXAMPLE 3

The effect of the composition of the coating solution and coating solution viscosity on the stability of active zones as demonstrated by resistance to interzone bleeding was studied using the method described below. Substrates were composed of 70/30 rayon/polyester blend cloth with an water/glycerin absorptive capacity of 1236%. Cloths were stencil coated in an alternating stripewise pattern as illustrated in FIG. 3 with using coating solutions described in tables 7 through 10. Active zones and non-active zones had equal total coating and carrier solvent coating weight concentrations. The interzone bleed results according to visual detection are shown in table 3.

TABLE 3

| Cloth composition | Coating solution Non-active zone | Coating solution Active zone | Coating weight % | Carrier solvent wt % | Coating solution viscosity (cps) | Interzone bleed detected | Inventive (I)/ Comparative (C) |
|---|---|---|---|---|---|---|---|
| 70/30 rayon polyester[4] | Table 9 | Table 8 | 100 | 89 | Water thin | No | I |
| 70/30 rayon polyester[4] | 10 | 11 | 100 | 78 | 5,000 | No | I |

[4]PGI hydroentangled 7086

TABLE 4

(Solution I)

| Ingredient name | W/W % |
|---|---|
| Deionized water | 25.50 |
| Glycerin | 25.00 |
| Polyquaternium 4, | 0.15 |
| Polyquaternium 10, | 0.40 |
| cocamidopropyl betaine, 30% active in water | 18.23 |
| decyl polyglucoside, 50% active in water | 11.15 |
| sodium lauroyl sarcosinate, 30% active in water | 18.23 |
| Na lauryl lactylate | 0.20 |
| silicone quaternium-8, 40% in water | 0.50 |
| Fragrance | 0.30 |
| Sodium A1 (5%), lactic acid (5%), potassium lactate (5%), and urea (1%) in water. | 0.10 |
| soya sterol | 0.01 |
| Cholesterol | 0.01 |
| Vitamin E acetate (BASF) | 0.01 |
| Vitamin A palmitate | 0.01 |
| Glydant Plus Liquid | 0.20 |
| | 100.00 |

TABLE 5

(Solution II)

| Ingredient name | W/W % |
|---|---|
| Deionized water | 25.49 |
| Glycerin | 25.00 |
| Polyquaternium 4 | 0.15 |
| Polyquaternium 10 | 0.40 |
| Cocamidopropyl betaine, 30% active in water | 18.23 |
| decyl polyglucoside, 50% active in water | 11.15 |
| sodium lauroyl sarcosinate, 30% active in water | 18.23 |
| Na lauryl lactylate | 0.20 |
| Silicone quaternium-8, 40% in water | 0.50 |
| Fragrance | 0.30 |
| Sodium 5-oxo-dl-proline (5%), lactic acid (5%), potassium lactate (5%), and urea (1%) in water. | 0.10 |
| Soya sterol | 0.01 |
| Cholesterol | 0.01 |
| Vitamin E acetate | 0.01 |
| Vitamin A palmitate | 0.01 |
| Blue 1 | 0.008 |
| Yellow 5 | 0.002 |
| Glydant Plus Liquid | 0.20 |
| | 100.00 |

TABLE 6

Solution III

| Ingredient Name | % in formula |
|---|---|
| Vinyl dimethicone crosspolymer | 51.9 |
| Cetyl dimethicone copolyol | 0.75 |
| Fragrance | 0.05 |
| Menthyl lactate | 0.1 |
| Menthoxypropane diol | 0.08 |
| Isopulegol | 0.02 |
| Tocopherol acetate | 0.1 |
| Deionized water | 3.0 |
| Dimethyl isosorbide | 2.0 |
| PEG-4 | 10.5 |
| Propylene glycol, USP | 20.5 |
| Ascorbic acid, USP | 5.0 |
| Soluble collagen | 1.0 |
| Tapioca flour | 5.0 |

TABLE 7

Solution IV

| Ingredient | Wt. % |
|---|---|
| Deionized water | 30.0 |
| Ethanol | 66.0 |
| Salicylic acid | 4.0 |

TABLE 8

| Ingredient Name | W/W % |
|---|---|
| Deionized water | 67.45 |
| Na lauryl lactylate | 0.50 |
| DL-Panthanol | 0.05 |
| Glycerin | 3.00 |
| Glydant Plus | 0.10 |
| Hydroxyethyl Cetyldimonium Phosphate, 30% in water | 1.00 |
| PEG 75 soy glycerides | 1.00 |
| Silicone quatenium-8, 40% in water | 2.00 |
| Polyquaterniuim 11, 20% in water | 0.50 |
| Sodium laureth sulfate (2EO), 30% in water | 6.00 |
| Sodium C14-16 olefin sulfonate, 30% in water | 6.00 |
| Cocamidopropyl betaine, 30% in water | 6.00 |
| Sodium lauroamphoacetate, 30% in water | 5.00 |
| Polysorbate 80 | 1.00 |
| Polysorbate 20 | 0.15 |
| Witch Hazel extract | 0.01 |
| Hops extract | 0.01 |
| Rosemary extract | 0.01 |
| Swertia Japonica | 0.01 |
| Camelia Oleiferra extract | 0.01 |
| Gentisic acid | 0.00010 |

TABLE 8-continued

| Ingredient Name | W/W % |
|---|---|
| Fragrance | 0.20 |
| FD&C green 3 | 0.0050 |

TABLE 9

| Ingredient Name | W/W % |
|---|---|
| Deionized water | 67.45 |
| Na lauryl lactylate | 0.50 |
| DL-Panthanol | 0.05 |
| Glycerin | 3.00 |
| Glydant Plus | 0.10 |
| Hydroxyethyl Cetyldimonium Phosphate, 30% in water | 1.00 |
| Peg 75 soy glycerides | 1.00 |
| Silicone quaternium-8, 40% in water | 2.00 |
| Polyquaterniuim 11, 20% in water | 0.50 |
| Sodium laureth sulfate (2eo), 30% in water | 6.00 |
| Sodium C14-16 olefin sulfonate, 30% in water | 6.00 |
| Cocamidopropyl betaine, 30% in water | 6.00 |
| Sodium lauroamphoacetate 30% in water | 5.00 |
| Polysorbate 80 | 1.00 |
| Polysorbate 20 | 0.15 |
| Witch Hazel extract | 0.01 |
| Hops extract | 0.01 |
| Rosemary extract | 0.01 |
| Swertia Japonica | 0.01 |
| Camelia Oleiferra extract | 0.01 |
| Gentisic acid | 0.00010 |
| Fragrance | 0.20 |

TABLE 10

| Ingredient name | W/W % |
|---|---|
| Deionized water | 28.27 |
| Glycerin | 22.00 |
| Decyl polyglucoside, 50% active in water | 9.50 |
| Cationic guar (Jaguar C14S) | 0.70 |
| Cationic guar (Jaguar HP60) | 0.30 |
| Citric Acid | 0.20 |
| Sodium lauroyl sarcosinate, 30% active in water | 16.50 |
| Cocamidopropyl betaine, 30% active in water | 16.50 |
| Sodium 5-oxo-dl-proline (5%), lactic acid (5%), potassium lactate (5%), and urea (1%) in water. | 0.10 |
| Cholesterol | 0.01 |
| Vitamin E acetate | 0.01 |
| Vitamin A palmitate | 0.01 |
| Petrolatum | 4.50 |
| Stearic acid | 1.00 |
| Fragrance | 0.20 |
| Glydant Plus Liquid | 0.20 |

TABLE 11

| Ingredient name | W/W % |
|---|---|
| DI water | 28.27 |
| Glycerin | 22.00 |
| Decyl polyglucoside, 50% active | 9.50 |
| Cationic guar (Jaguar C14S) | 0.70 |
| Cationic guar (Jaguar HP60) | 0.30 |
| Citric Acid | 0.20 |
| Sodium lauroyl sarcosinate, 30% active in water | 16.50 |
| Cocamidopropyl betaine, 30% in water | 16.50 |
| Sodium 5-oxo-dl-proline (5%), lactic acid (5%), potassium lactate (5%), and urea (1%) in water. | 0.10 |
| Cholesterol | 0.01 |
| Vitamin E acetate | 0.01 |
| Green 3 | 0.005 |
| Vitamin A palmitate | 0.01 |

TABLE 11-continued

| Ingredient name | W/W % |
|---|---|
| Petrolatum | 4.50 |
| Stearic acid | 1.00 |
| Fragrance | 0.20 |
| Glydant Plus Liquid | 0.20 |

TABLE 12

| Ingredient name | W/W % |
|---|---|
| DI water | 25.43 |
| Glycerin | 25.00 |
| Polyquaternium 4 | 0.15 |
| Polyquaternium 10 | 0.40 |
| Cocamidiopropyl betaine, 30% active in water | 18.23 |
| Decyl polyglucoside, 50% active in water | 11.15 |
| Sodium lauroyl sarcosinate, 30% active in water | 18.23 |
| Na lauryl lactylate | 0.20 |
| Silicone quatenium-8, 40% in water | 0.50 |
| Essential Oil Blend | 0.10 |
| Green Tea Extract | 0.10 |
| Roman Chamomile Extract | 0.10 |
| Aloe Vera Extract | 0.10 |
| Vitamin E acetate | 0.10 |
| Vitamin A palmitate | 0.01 |
| Glydant Plus Liquid | 0.20 |
|  | 100.00 |

TABLE 13

| Ingredient name | W/W % |
|---|---|
| DI water | 24.93 |
| Glycerin | 25.00 |
| Polyquaternium 4 | 0.15 |
| Polyquaternium 10 | 0.40 |
| Cocamidiopropyl betaine, 30% active in water | 18.23 |
| Decyl polyglucoside, 50% active in water | 11.15 |
| Sodium lauroyl sarcosinate, 30% active in water | 18.23 |
| Na lauryl lactylate | 0.20 |
| Silicone quaternium-8, 40% in water | 0.50 |
| Essential Oil Blend | 0.10 |
| Green Tea Extract | 0.10 |
| Roman Chamomile Extract | 0.10 |
| Aloe Vera Extract | 0.10 |
| Vitamin E acetate | 0.10 |
| Vitamin A palmitate | 0.01 |
| FD&C Green number 3 | 0.005 |
| Covasorb | 0.50 |
| Glydant Plus Liquid | 0.20 |
|  | 100.00 |

TABLE 14

| Ingredient name | Raw Mat. # | W/W % |
|---|---|---|
| DI water | R50332 | 25.98 |
| Glycerin | R50078 | 25.00 |
| Cocamidopropyl betaine, 30% active in water | R62627 | 18.23 |
| Decyl polyglucoside, 50% active-in water | R52110 | 11.15 |
| Sodium lauroyl sarcosinate, 30% active in water | R51752 | 18.23 |
| Na lauryl lactylate | R51177 | 0.20 |
| Silicone quaternium-8, 40% in water | R51574 | 0.50 |
| Essential Oil Blend (AC11203) | R57688 | 0.10 |
| Grren Tea Extract | R51530 | 0.10 |
| Roman Chamomile Extract | R51230 | 0.10 |
| Aloe Vera Extract | R51619 | 0.10 |
| Vitamin E acetate | R51044 | 0.10 |

TABLE 14-continued

| Ingredient name | Raw Mat. # | W/W % |
|---|---|---|
| Vitamin A palmitate | R50786 | 0.01 |
| Glydant Plus Liquid | R51520 | 0.20 |
| | | 100.00 |

TABLE 15

| Ingredient name | Raw Mat. # | W/W % |
|---|---|---|
| DI water | R50332 | 25.48 |
| Glycerin | R50078 | 25.00 |
| Cocamidopropyl betaine, 30% active in water | R62627 | 18.23 |
| Decyl polyglucoside, 50% active-in water | R52110 | 11.15 |
| Sodium lauroyl sarcosinate, 30% active in water | R51752 | 18.23 |
| Na lauryl lactylate | R51177 | 0.20 |
| Silicone quaternium-8, 40% in water | R51574 | 0.50 |
| Essential Oil Blend (AC11203) | R57688 | 0.10 |
| Grren Tea Extract | R51530 | 0.10 |
| Roman Chamomile Extract | R51230 | 0.10 |
| Aloe Vera Extract | R51619 | 0.10 |
| Vitamin E acetate | R51044 | 0.10 |
| Vitamin A palmitate | R50786 | 0.01 |
| FD&C Green number 3 | | 0.005 |
| Covasorb | | 0.50 |
| Glydant Plus Liquid | R51520 | 0.20 |
| | | 100.00 |

Experimental Test Methods:

Dynamic Active Zone Component Depletion Percentage.

The dynamic active zone depletion percentage of a given active zone component is calculated by quantifying the active zone component deposited on the active zone of the substrate on the basis of substrate weight, sealing the wiping article in a plastic bag for 7 days at 23 C, and repeating the quantification test at the end of that time. The percent depletion is calculated as follows:

$$\% \text{ dynamic active zone depletion} = \frac{\text{Initial conc.} - \text{final conc.}}{\text{Initial conc.}} \times 100$$

The foregoing description and examples illustrate selected embodiments of the present invention. In light thereof variations and modifications will be suggested to one skilled in the art, all of which are within the scope and spirit of this invention.

We claim:

1. A disposable, single use personal care article, comprising:
   a) a water insoluble substrate consisting of a single layer having an active zone, a non-active zone adjacent to the active zone, and an interface therebetween;
   b) a coating composition with a melting point below 30 C, the coating composition containing at least one benefit agent selected from an active agent, a conditioning agent, an aesthetic agent and a mixture thereof for treating the skin or hair, the coating composition being releasably associated with the active zone;
   c) a carrier solvent with an effective diffusion rate within the water insoluble substrate, the carrier solvent being selected from water, a water miscible compound, an oil, an oil soluble compound, and a mixture thereof; wherein the coating composition is dissolved, dispersed, or emulsified in the carrier solvent; wherein the carrier solvent in the active or non-active zone is in a concentration range of about 5 to about 160 wt. % based on the substrate; and
   d) wherein the effective diffusion rate of the carrier solvent across the interface is substantially identical to the diffusion rate of the carrier solvent adjacent to the interface.

2. The personal care article of claim 1 wherein the active zone contains a higher total benefit agent concentration then the non-active zone based on the weight of the substrate.

3. The personal care article of claim 1 wherein the benefit agent in the active zone is in the concentration range of about 0.01% to about 100% by weight based on the substrate.

4. The personal care article of claim 1 wherein the dynamic active zone depletion percentage of the benefit agent is less than about 50% based on the weight of the substrate.

5. The personal care article of claim 1 wherein the water insoluble substrate comprises one layer of a woven or non-woven fabric and the benefit agent is deposited in a pattern on the fabric.

6. The personal care article of claim 1 further comprising a plurality of layers.

7. The personal care article of claim 1 wherein the total coating weight in the active zone is in the concentration range of about 1% to about 400% by weight based on the substrate.

8. The personal care article of claim 1 further comprising at least one lathering surfactant contained in the non-active zone.

9. The personal care article of claim 8 wherein the lathering surfactant is in the concentration range of about 2% to about 100% by wt. based on the substrate and the active zone contains less than about 20 wt. % of lathering surfactant.

10. The personal care article of claim 1 wherein the ratio of carrier solvent to article absorptive capacity in the active or non-active zone is below about 0.13.

11. The personal care article of claim 5 wherein the at least one layer of a woven or non-woven fabric comprises a hydrophilic fabric.

12. The personal care article of claim 11 wherein the hydrophilic fabric is a blend of cellulosic and non-cellulosic fibers.

13. The personal care article of claim 12 wherein the hydrophilic fabric comprises rayon and polyester.

14. The personal care article of claim 13 wherein the hydrophilic fabric comprises rayon and polyester in the concentration ratio range of about 9.8 to about 1.0.

15. The personal care article of claim 11 wherein the hydrophilic fabric contains a plurality of apertures having a major axis diameter in the range of about 0.5 to about 10 mm and wherein the apertures are distributed on the substrate in the range of about 1 to about 10 per linear centimeter.

16. The personal care article of claim 11 wherein the hydrophilic fabric comprises at least one layer of fibers made by a process selected from hydroentangled, wet laid, dry laid, spun bonded, needle punched, and air laid.

17. The personal care article of claim 8 wherein the concentration ratio of the sum of benefit agents and lathering surfactant to the substrate is less than about 5.0 based on the weight of the substrate.

18. The personal care article of claim 1 wherein the at least one active agent is selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; and a mixture thereof.

19. The personal care article of claim 1 further comprising at least one water-soluble or water dispersible indicator in contact with the benefit agent in the active zone of the substrate in an amount sufficient to impart a distinct outward appearance to the active zone which differs from the adjacent zone, the outward appearance being selected from a color dominant wavelength, color or shade density, and surface reflectivity, and whereby the outward appearance of the active zone will vary indicating the transfer of the benefit agent to the user's skin or hair when the article is exposed to water.

20. The personal care article of claim 19 wherein the indicator is a cosmetically suitable dye that either is at least partially solvated, dispersed, or suspended in the carrier solvent or that is substantively bonded to the water insoluble substrate.

21. The personal care article of claim 19 wherein the indicator is selected from a permanent dye; a pH sensitive dye; an encapsulated dye adjacent to a barrier layer; a leuco dye; and a dye substantively bonded to the active agent, conditioning agent, or aesthetic agent.

22. The personal care article of claim 21 wherein the encapsulated dye is released by mechanical rupture, dissolution, or permeation of the barrier layer by a substance selected from water, active agents, conditioning agents, aesthetic agents, lathering surfactants, water miscible solvents, oils, oil soluble solvents, or a mixture thereof.

23. The personal care article of claim 1 wherein the carrier solvent comprises a compound selected from water, a polyhydric alcohol, a polyol, and a blend thereof.

24. The personal care article of claim 1 wherein the carrier solvent contains at least 20% by weight of water.

25. The personal care article of claim 1 wherein the active zone has a distinct pattern selected from stripes, geometric shapes, amorphous shapes, symbols, indicia and a combination thereof.

26. The personal care article of claim 1 wherein the active zone and the adjacent zone are oriented as stripes with substantially parallel boundary lines.

27. A method of manufacturing a disposable, single use personal care article, comprising the steps of:
   a) preparing a composition including at least one benefit agent selected from an active agent, a conditioning agent, and an aesthetic agent;
   b) adding in any sequence to the composition in (a) a lathering surfactant, a carrier solvent, and a visual indicator;
   c) applying the composition prepared in (b) to in a pattern to a hydrophilic substrate using a method selected from coating, spraying, splashing, dipping, slot die coating, and stencil coating; and
   d) adjusting in any sequence the water content of the article in the concentration range of about 5 to about 50% by weight based on the substrate; wherein the hydrophilic substrate containing the visual indicator contains less than about 20% of the lathering surfactant based on the substrate in the patterned area.

28. The method of claim 27 wherein the pattern is selected from stripes, geometric shapes, amorphous shapes, symbols, indicia and a combination 29. A method of depositing a benefit agent onto the skin or hair comprising the steps of:
   a) providing an article comprising
      i) a water insoluble substrate consisting of a single layer having an active zone and a nonactive zone adjacent to the active zone;
      ii) a coating composition with a melting point below 30 C, the coating composition containing at least one benefit agent selected from an active agent, a conditioning agent, an aesthetic agent and a mixture thereof for treating the skin or hair, the coating composition being releasably associated with the active zone; the active zone releasably containing the benefit agent,
      iii) a carrier solvent with an effective diffusion rate within the water insoluble substrate, the carrier solvent being selected from water, a water miscible compound, an oil, an oil soluble compound, and a mixture thereof; wherein the coating composition is dissolved, dispersed, or emulsified in the carrier solvent; wherein the carrier solvent in the active or non-active zone is in a concentration range of about 5 to about 160 wt. % based on the substrate; and
      iv) at least one water-soluble or water dispersible visual indicator in contact with the benefit agent in the active zone in an amount sufficient to impart a distinct outward appearance to the active zone, the outward appearance being selected from a color dominant wavelength, color or shade density, and surface reflectivity whereby the outward appearance will vary indicating the transfer of the benefit agent to the user's skin or hair when the article is exposed to water;
   b) wetting the article with water; and
   c) applying the article to the skin or hair whereby the benefit agent is deposited thereon at a level between about 0.01 μg/cm$^2$ to about 20 μg/cm$^2$.

* * * * *